(12) United States Patent
Kaestle et al.

(10) Patent No.: US 8,418,693 B2
(45) Date of Patent: Apr. 16, 2013

(54) METHOD AND DEVICE FOR EVALUATION OF SPIROGRAPHIC AND GAS EXCHANGE DATA

(75) Inventors: Sigfried Kaestle, Nufringen (DE); Andreas Schlack, Gaeufelden OT Tailfingen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 780 days.

(21) Appl. No.: 12/531,348

(22) PCT Filed: Mar. 13, 2008

(86) PCT No.: PCT/IB2008/050911
§ 371 (c)(1),
(2), (4) Date: Sep. 15, 2009

(87) PCT Pub. No.: WO2008/114172
PCT Pub. Date: Sep. 25, 2008

(65) Prior Publication Data
US 2010/0101577 A1   Apr. 29, 2010

(30) Foreign Application Priority Data

Mar. 16, 2007 (EP) .................................... 07104315

(51) Int. Cl.
A61B 5/08 (2006.01)
A61B 5/087 (2006.01)
A61B 5/091 (2006.01)

(52) U.S. Cl.
USPC ............. 128/204.22; 128/204.18; 128/204.26

(58) Field of Classification Search ............. 128/204.22, 128/204.18, 204.21, 204.23; 600/529, 532, 600/538
See application file for complete search history.

(56) References Cited

U.S. PATENT DOCUMENTS

| | | | |
|---|---|---|---|
| 3,729,000 A * | 4/1973 | Bell .......................... | 128/204.21 |
| 5,103,814 A * | 4/1992 | Maher ....................... | 128/204.18 |
| 5,971,934 A | 10/1999 | Scherer et al. | |
| 6,099,481 A | 8/2000 | Daniels et al. | |
| 2001/0029339 A1 | 10/2001 | Orr et al. | |
| 2002/0082511 A1 | 6/2002 | Carlebach et al. | |
| 2003/0214409 A1 * | 11/2003 | Hickle ......................... | 340/573.1 |
| 2004/0216740 A1 * | 11/2004 | Remmers et al. ........ | 128/204.18 |

(Continued)

FOREIGN PATENT DOCUMENTS

WO   02096289 A1   12/2002
WO   20060182237 A1   2/2006

OTHER PUBLICATIONS

Cummings EG, Blevins WV, Craig FN. Measurement of external dead space with a new flowmeter. J Appl Physiol. Jul. 1960:15:741-742.*

(Continued)

*Primary Examiner* — Justine Yu
*Assistant Examiner* — Christopher Miller

(57) ABSTRACT

The invention provides a method for obtaining and evaluating spirographic and gas exchange data, involving measuring a concentration of a breathing gas $gc(Vx)$ for a plurality of volumes $Vx$ of breathing gas mix, wherein the measuring is performed on inhaled breathing gas mix, further involving determining an apparatus dead space ApDS, of breathing gas mix in the apparatus not taking part in gas exchange, by evaluating the measured concentrations $gc(Vx)$ as a function of the volume V of the inhaled breathing gas mix. The use of inhaled breathing gas mix allows to determine the apparatus dead space, which is an important parameter when evaluating ventilation efficiency and the like. Furthermore, the invention provides a method in which inhalation and exhalation parts of a spirogram are synchronized, by matching features thereof, in order to further improve the accuracy of gas exchange volumes and derived data. Finally, the invention provides a spirographic device and a patient ventilation apparatus, incorporating the present method.

10 Claims, 3 Drawing Sheets

U.S. PATENT DOCUMENTS

| | | | |
|---|---|---|---|
| 2005/0028817 A1* | 2/2005 | Jaffe et al. | 128/200.24 |
| 2007/0107728 A1* | 5/2007 | Ricciardelli et al. | 128/204.21 |
| 2007/0221224 A1* | 9/2007 | Pittman et al. | 128/204.22 |
| 2007/0240718 A1* | 10/2007 | Daly | 128/204.22 |
| 2008/0127977 A1* | 6/2008 | Orr et al. | 128/204.22 |

OTHER PUBLICATIONS

Den Buijs, J.O., et al.; Bayesian tracking of a nonlinear model of the capnogram; 2006; IEEE Engineering in Medicine and Biology; pp. 4; abstract.

Heller, J., et al.; An algebraic solution to dead space determination according to Fowler's graphical method; 1999; Computers and Biomedical Research; 32(2)abstract.

Kars, A. H., et al.; Dead Space and slope indices from the expiratory carbon dioxide tension-volume curve; 1997; Eur. Respir. J.; 10:1829-1836.

Fowler, W.S.; Lung Function Studies. II. The Respiratory Dead Space; 1948; Am. J. Physiol.; 154:405-416.

* cited by examiner

METHOD AND DEVICE FOR EVALUATION OF SPIROGRAPHIC AND GAS EXCHANGE DATA

FIELD OF THE INVENTION

The invention relates to methods and devices for the evaluation of spirographic and gas exchange data, to obtain more information and/or more accurate information therefrom.

BACKGROUND OF THE INVENTION

In the state of the art, it is known to obtain spirographic information. In known spirographic methods, such as described in WO2006/0182237, the concentration of a gas in exhaled breathing gas mix, often carbon dioxide or oxygen, is measured for a plurality of values of expired volumes. In this way, one obtains the gas concentration as a function of volume. From this function, one can estimate the airway dead space, which relates to a volume of breathing gas mix that is moved through the (upper) airway, such as the windpipe and bronchi, does not enter the alveoli, and hence does not take part in the gas exchange. Additionally, it relates to alveolar dead space, which is the volume of air that remains in the alveoli, even when exhaling to the max. Many methods have been designed to determine these dead spaces, such as by Fowler, in "The Respiratory Dead Space", Am J Physiol 154, 405-416 (1948).

By means of these dead spaces, and of course other information, one can monitor the respiratory processes in a human or animal subject, in order e.g. to establish its health state and changes therein.

In practice, it has been found that the obtained information is not always sufficient or sufficiently accurate. For example, sometimes a correct diagnosis, monitoring, or adequate ventilation of the subject is not reliably possible.

OBJECT OF THE INVENTION

It is an object of the invention to improve the known spirographic and gas exchange methods and apparatus, to allow more accurate information to be obtained.

SUMMARY OF THE INVENTION

To achieve the above object, in a first aspect, the invention provides a method for obtaining and evaluating spirographic data, comprising measuring a concentration of a breathing gas $gc(Vx)$ for a plurality of values of a volume Vx of breathing gas mix, for an animal or human being, with a suitable apparatus, wherein the measuring is performed on inhaled breathing gas mix, further comprising determining an apparatus dead space ApDS, of breathing gas mix in the apparatus not taking part in gas exchange, by evaluating the measured concentrations $gc(Vx)$ as a function of the volume V of the inhaled breathing gas mix.

The present invention utilizes the inspired part of a spirogram, instead of or in addition to the expired part, to give useful additional information. In particular, it allows to determine an apparatus dead space ApDS, which relates to (inter alia) tubing, filter between a gas sensor and a Y-piece towards a ventilator apparatus. This is also a volume that is moved when breathing, or ventilating, but which does not partake in the gas exchange and which is not determined with the known methods or apparatus.

The part of the method to determine the ApDS itself can be chosen in accordance with any known method to determine a respiratory dead space, as will be exemplified below. And such method is not deemed to lie at the heart of the invention. This is rather realizing that the apparatus dead space is an important quantity, and realizing that this quantity may be determined with the help of the inhaled part of the spirogram. Similarly, any known apparatus suitable for obtaining a spirograph, in particular the inhaled part, may be used in the method.

Below, particular embodiments will be disclosed, which are only deemed examples of the general inventive principle.

In an embodiment, the step of determining ApDS comprises applying a mathematical operation to the measured concentrations as a function of volume. In particular, said mathematical operation comprises determining a $gc(V1)$ at a first volume V1 at the beginning of inhaling, determining a $gc(V4)$ at a second volume V4 at the end of inhaling, and determining the ApDS as the difference between V1 and a volume V2 at which $gc(V2)=(gc(V4)+gc(V1))/2$, also coming down to about $0.5\, gc(V1)$. The various volumes identified above may also be found in FIG. 1b. Note that these volumes may be plotted as is usual, i.e. the origin being zero exhaled volume, and exhaled volume is plotted on the positive abscissa. Of course, if a different way of plotting is used, the skilled person will accordingly use minus signs etc. where needed. The above is one of the simplest (mathematical) methods to determine the ApDS. Alternatively, one could use a method similar to Fowler's, i.e. fit a straight line to the data corresponding to the volumes of deepest exhaling, but in this case at the beginning of inhaling, and determine ApDS as the volume where the areas r and s in FIG. 1b are equal. Many other methods have been found in the state of the art to determine airway dead space, such as in the mentioned document WO2006/0182237. All such methods could be applied to determine the apparatus dead space, in accordance with the present invention.

In the present context, it is possible that the start and end points of consecutive breaths do not match, as individual breaths need not be equally deep. However, one could take average values. Furthermore, it is not always necessary to determine the final value of the gas concentration, i.e. at the end of inhaling, because in the majority of cases, this final value will be substantially equal to the value for fresh gas, often room air. Such value could be determined once. Of course, for the most accurate measurements, the final value is also measured.

Also disclosed are embodiments further comprising the steps of measuring $gc(Vx)$ for a plurality of values of a volume Vx of exhaled breathing gas mix and of determining an airway dead space AwDS and/or alveolar dead space AlDS by evaluating said measured concentrations. By combining the present invention with such a step, additional information about dead spaces may be obtained, which is useful when setting up a ventilation scheme for a patient, evaluating a spirogram of a patient, and so on. The airway dead space and/or alveolar dead space may be determined with the aid of any known method, such as the ones mentioned above and/or in e.g. WO2006/0182237.

In a particular embodiment, the method further comprises the step of determining a ventilated volume VV as $VV=V1-(ApDS+AwDS)$, and preferably comprising the step of determining a ventilation efficiency VE as $VE=VV/V1$. herein, V1 equals a total tidal volume, i.e. the difference between maximum measured volume and minimum measured volume. By including the ApDS, more accurate results may be obtained. This may be very important when establishing breathing efficiency of a subject, or ventilating a subject. For example, the effective volume of a breath to remove CO2 was only 40% of the total volume used to blow the lungs. This causes unwanted stress on the lungs and can cause lung damage and prolong weaning.

It is to be noted that the breathing gas in the present invention could be e.g. carbon dioxide or oxygen, although others such as water vapour are not excluded. In an embodiment, the concentrations of both carbon dioxide and oxygen are measured and evaluated. Preferably, at least one of ApDS, AwDS and AIDS is determined for both a corresponding oxyspirogram and a capnospirogram. This gives more accurate results, since the results for carbon dioxide may be compared to those for oxygen, or vice versa.

Further information may be obtained in a method according to the invention, wherein the total eliminated carbon dioxide or uptaken oxygen is determined from a combination of the inhaled and exhaled part of the spirographic data. As is known per se, these quantities may be determined from a spirogram by determining the area between the expired and inspired part of the spirogram.

In an important further embodiment, the method further comprises the step of synchronizing an exhaled part and an inhaled part of the spirographic data by optimum matching between said exhaled and inhaled parts at the Vmax end of the spirographic data. This is based on the insight that there may be a time delay between the measurements of volume and gas concentration, which may cause a shift of the gas concentration curves with respect to the volume. Realising that the "last" part, or end tidal volume part or Vmax part, of the exhaled breath will be rebreathed, this shows that the gas concentration in the corresponding rebreathed volume will show substantially the same features as that in the last part of the exhaled breath. Optimum matching then comes down to finding the point at which concentration measurement corresponds to that point of reversal of breathing, which is symmetrically midway between those corresponding features.

The way in which this matching is optimised may be selected according to any known technique. The selected way may depend on the way of displaying the measured values, if these are displayed at all. If displayed, the spirogram may e.g. show the exhaled and inhaled parts in a single diagram. In such a case, an optimum match may be obtained when the exhaled part is shifted to the left or right over a volume Vshift and the inhaled part over a corresponding volume −Vshift, such that one or more features in the plateau part, preferably a local extreme value in one of the two parts is brought into register with the corresponding feature in the other of the two parts. It is noted that such a feature need not be found in every breath. In that case, matching would be an inaccurate operation, and it is preferred to do this matching in a subsequent respiration that does show a feature, such as a dip in the gas concentration. Note that the apparatus dead space is a constant for the apparatus, and need be determined only once. Of course, if a new tubing, sensor or the like is used, this apparatus dead space could be determined anew. In the proximity of Vmax the inspired and expired parts are mirrored with respect to a vertical line at Vmax.

A basic way of mirroring and matching is of course by hand, judging with the eye which is the midpoint in the spirogram. Alternatively, mathematical functions could be used, e.g. those that determine the quality of a match between curves by a least sum of squared differences or the like. The skilled person will know how to implement this according to his demands.

In a second aspect, the invention also relates to a spirographic device for obtaining and evaluating spirographic data, comprising a gas volume meter for measuring a volume Vx of at least inhaled breathing gas mix, a gas measuring probe for measuring a concentration gc(Vx) of a breathing gas in said volume of breathing gas mix, wherein the device is arranged to perform a method according to the invention. Such a device can give accurate results for at least the apparatus dead space ApDS. Preferably, the device comprises a computer arranged to perform a suitable mathematical operation on the obtained spirographic data.

Herein, the gas volume meter is often a flow meter, that determines the flow of passing breathing gas mix.

In particular, the device, and/or the computer, is arranged to couple a measured gas concentration to a corresponding volume measurement, as is known in the art per se. Also, the device may be arranged for measuring carbon dioxide and/or oxygen, and/or another gas such as water vapour. A suitable probe or sensor is available.

The device and/or computer are arranged to carry out a mathematical operation on the spirographic data, for obtaining at least a value of the apparatus dead space, according to the invention. Such a method could be according to any method described above.

Of course, both in the method and in the device, it is provided that the values are stored at least long enough to perform the desired action upon them. A suitable memory is incorporated.

The invention also relates to a patient ventilation device, comprising a tubing to be inserted into a patient's airway, a controllable breathing gas supply means connected to said tubing and a spirographic device according to the invention. Such a ventilation device may make good use of the invention, in that the breathing efficiency may be determined more accurately and especially in that the ventilation efficiency may be set more expediently. This not only improves the patient's well-being, but could also prevent lung damage. In this ventilation device, the spirographic device allows to establish an apparatus dead space at any use.

The invention also relates to a patient ventilation device, comprising a tubing to be inserted into a patient's airway, a controllable breathing gas supply means connected to said tubing, wherein the volume of breathing gas mix as supplied by the ventilation device is adjustable taking into account a predetermined apparatus dead space ApDS as determined with the method according to the invention. In this device, use is made of the circumstance that the apparatus dead space need only be set once, at least if the apparatus is not modified. Hence, the manufacturer or first user may determine such apparatus dead space once, and set the device accordingly. For example, this volume is subtracted from the indicated ventilation volume. Of course, if the device is modified, such as when tubing or a sensor is replaced, a new gauge measurement may be carried out, such as according to the method or with the aid of the spirographic device of the invention.

The invention also relates to method of obtaining and evaluating spirographic data, comprising measuring a concentration of a breathing gas gc(Vx) for a plurality of values of a volume Vx of breathing gas mix, for an animal or human being, with a suitable apparatus, both for breathing in and for breathing out until an end tidal volume Vmax, further comprising the step of synchronizing an exhaled part and an inhaled part of the spirographic data by optimum matching between said exhaled and inhaled parts at the Vmax end of the spirographic data. This is simply a method of determining the amount a breathing gas is exchanged, such as oxygen uptake or carbon dioxide elimination, but now without the feature of determining apparatus dead space, which is irrelevant here. Since synchronisation allows a more accurate coupling between volume and the corresponding gas concentration, more accurate values for such gas exchange may be obtained.

Furthermore, all combinations with other features mentioned in the description above are possible.

DETAILED DESCRIPTION OF EXAMPLES

Figure 1A:
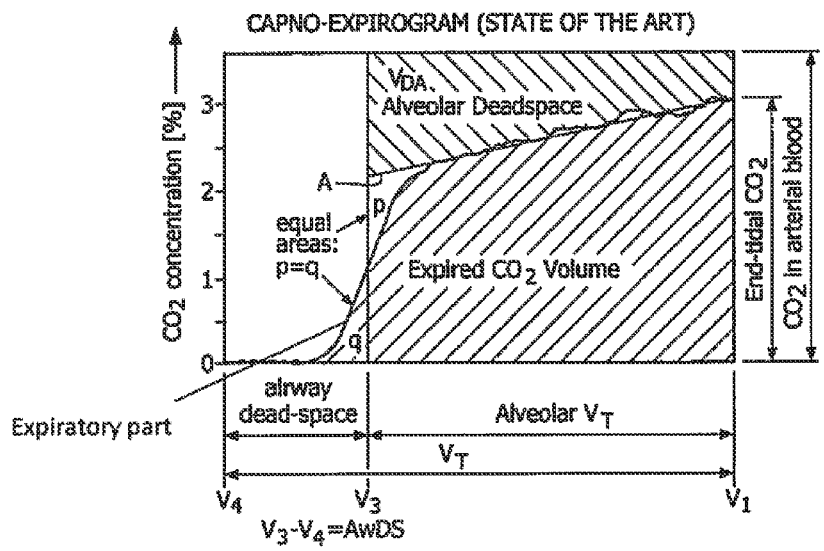
FIG. 1a shows schematically a capnospirogram, the expiration part of a breath cycle (also known as single-breath CO2)

FIG. 1a shows schematically a capnospirogram $V_T$, plotting CO2 concentration versus the volume, in arbitrary units, of exhaled breathing gas mix. The known, general features of the diagram are e.g. the low plateau for low volumes, indicating air from the subject's non-alveolar airway, such as the bronchi, followed by a steep rise, which indicates the mixing in of alveolar air, and the substantially linear slope at the end, which indicates the increasing CO2 concentration during breathing out of additional alveolar air.

In order to obtain a value for the total expired volume of CO2, one can e.g. apply a method in which a straight line A, with a slope s as a fitting parameter, is fitted to the substantially linear part. The second step is to find the volume V3 for which the measured areas q and p, as indicated in the graph, are equal according to Fowler. The airway dead space equals said volume thus found. Note that other definitions are possible, such as the volume at which the gas concentration is 50% of its final, end tidal value, et cetera.

Figure 1B:
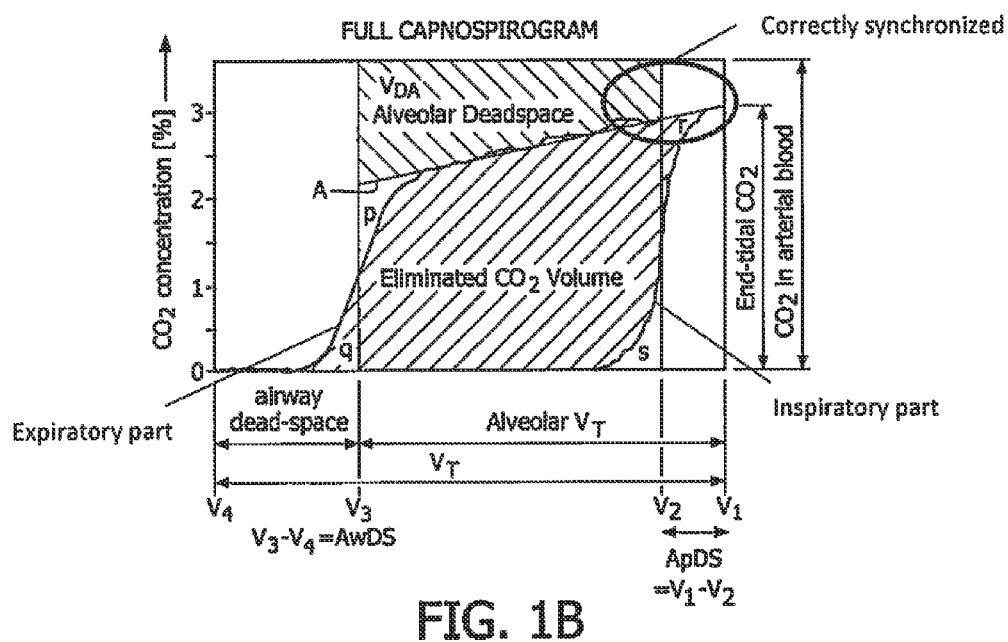
FIG. 1b shows a complete capnospirogram including the inspiratory part and apparatus deadspace

FIG. 1b shows a complete or full capnospirogram $V_T$, including both the inspiratory part and the expiratory part, as well as airway dead space, alveolar deadspace and apparatus deadspace.

In the graph, V1 denotes the volume at maximum breathing out, V2 denotes a volume corresponding to the apparatus deadspace when subtracted from V1, and air actually breathed in begins to pass the flow meter, V3 denotes a volume corresponding to the airway deadspace, and V4 denotes the starting point of breathing out. V4 could also be taken as the endpoint of breathing in other cases, as they need not be identical.

The expiratory part in the graph will be the same as that in FIG. 1a, but now the inspiratory part is included as the lower line in the graph. From the combination of both lines, the apparatus deadspace ApDS may be determined as V1−V2, where V2 is the volume at which the $CO_2$ concentration, starting from V1, has dropped to 50% of its value at V1, or alternatively to halfway between the CO2 concentrations at V1 and V4, i.e. beginning and end of breathing in.

Furthermore, alveolar deadspace and airway deadspace may be determined according to all known techniques. Also, eliminated CO2 volume may be determined as the area between the two lines.

In practice it is not always certain whether the concentration is associated with the correct volume, since often a sample is measured while separately a flow is measured. If there is a time delay between the two measurements, a correct association may not be obtained in some cases. This holds for both breathing in and breathing out.

Figures 2A, 2B:
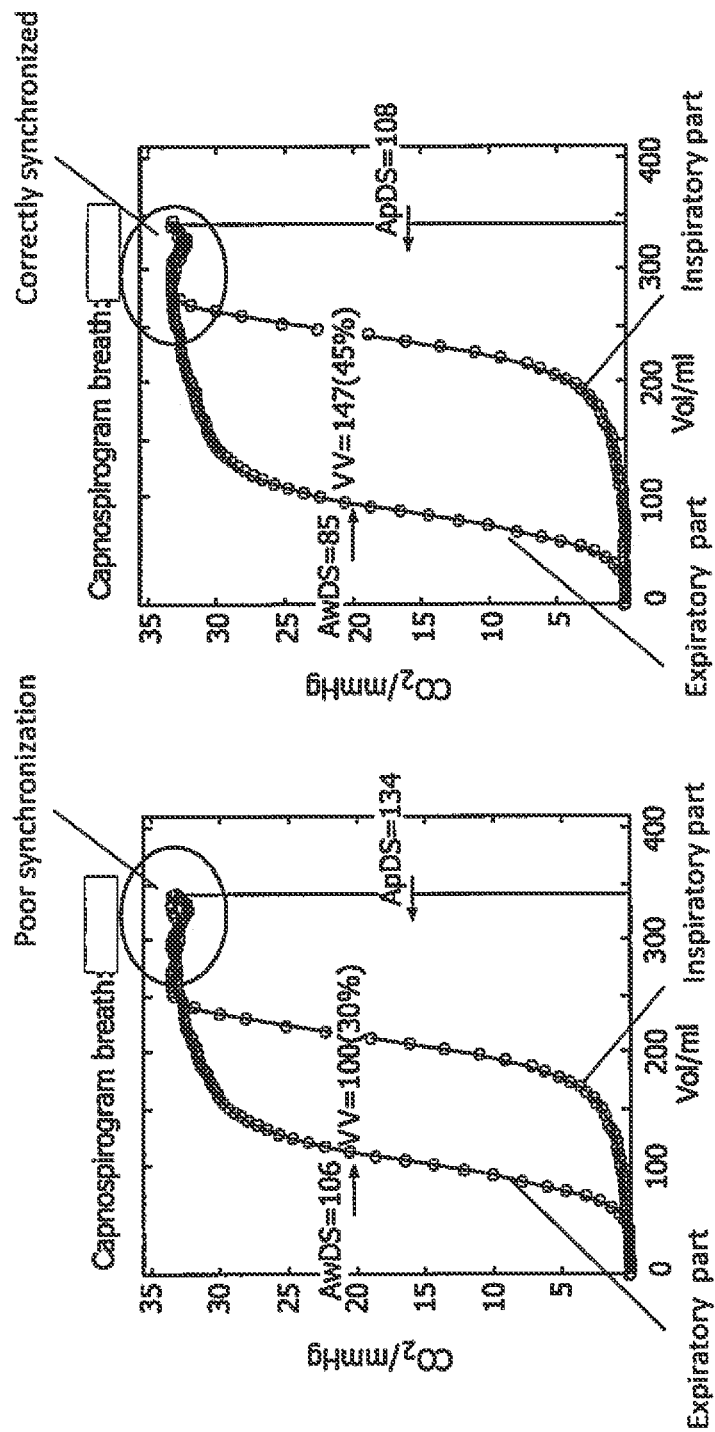
FIG. 2a shows an example of a poorly synchronised spirogram to the left.
FIG. 2b shows a spirogram correctly synchronised according to the invention, to the right.

FIG. 2a shows an example of such (apparent) poor synchronisation to the left, and FIG. 2b shows a correctly synchronised graph to the right.

Both graphs show a full capnospirogram, similar to the one in FIG. 1b, in which the CO2 concentration is plotted versus the volume of breathing gas mix that has passed the flow meter. The graph shows both an exhaling part on top in the graphs, and an inhaling part, as measured when going from "high" volume values back to zero volume, below in the graphs. In this way a closed loop is obtained. In the left graph are indicated values for airway dead space, apparatus dead space and alveolar volume. The airway dead space AwDS is determined e.g. according to the method described in connection with FIG. 1a. The apparatus dead space, ApDS, the measurement of which is an aspect of the present invention, may be determined with a similar method, but now for the inhaling (lower) part (refer to FIG. 1b). The amount of exhaled CO2 is determined as the surface area between the inhaled and exhaled graph parts. In the present case, the volumes were determined as 106 ml, 134 ml and 100 ml, respectively. The value of the alveolar volume of 100 ml corresponds to 30% of the total tidal volume and represents the effective volume range for CO2 elimination.

It was found that incorrect synchronisation of the gas concentration measurement and volume measurement can have severe effects on the determined quantities. In other words, in practice it occurred that values deemed to belong to the exhaling part actually should have been considered parts of the inhaling part of the FIG. 2. In the graph, this would be expressed as a shift of the inspired and expired graphs to the right and left along the horizontal volume axis. The graphs are shifted in opposite directions thus changing the enclosed area, the eliminated CO2, significantly.

The present invention corrects this phenomenon by correctly synchronising the two graph parts. Thereto, use is made of features in the high volume parts of the graph. In this case, for example, there is a dip in the concentration values, indicated in the circumscribed detail. Such detail will return in the inhaling part, for example due to rebreathing the same volume. In that case, synchronisation may be obtained by shifting the two parts over equal volumes and mirror symmetrically with respect to the maximum measured volume, such that the corresponding features of both parts overlap optimally.

This method, according to the invention, has been followed in the right part of the FIG. 2b, which shows the same measurements as for the graph to the left, but now synchronised such that the dips in the circumscribed detail in both parts overlap. Now the airway dead space (AwDS), the apparatus dead space (ApDS) and alveolar volume can be determined as 85 ml, 108 ml, and 147 ml, respectively. It is clear that there are large discrepancies between the synchronised values and the poorly synchronised values.

Figure 3:
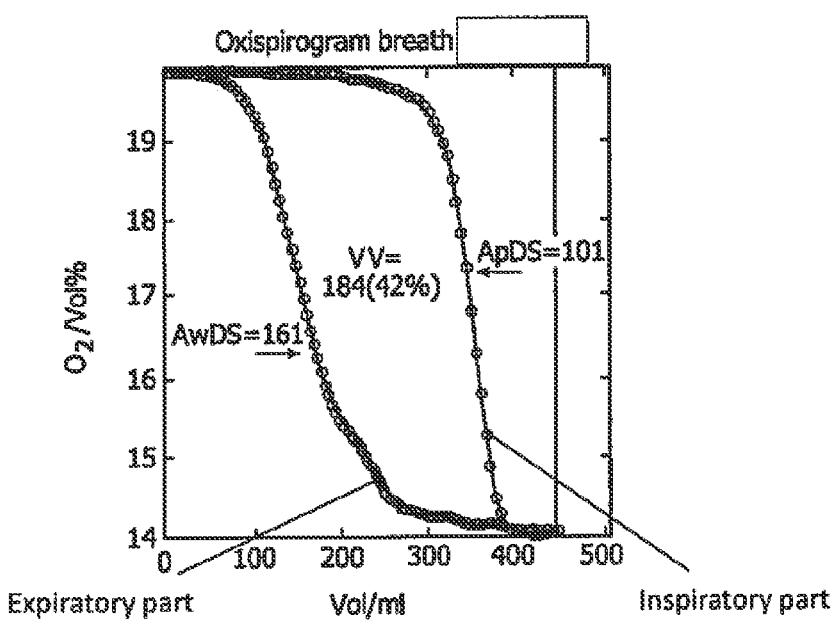
FIG. 3 shows an oxyspirogram, in which O2 concentration is plotted against volume.

FIG. 3 shows an oxyspirogram, in which O2 concentration is plotted against volume, again for an exhaled part (lower graph) and inhaled part (upper part). In similar ways as described for CO2 above, airway dead space (AwDS), apparatus dead space (ApDS), alveolar volume and oxygen uptake may be determined. Also, the same synchronisation steps may be performed for this oxyspirogram, to improve the accuracy and reliability. Note that the values for, in particular, apparatus dead space for CO2 and for O2 could differ, for example if different sensors and tubing are used. Similar measurements and methods are also possible for other respiratory gases, or even anaesthetic gases and so on.

Figure 4:
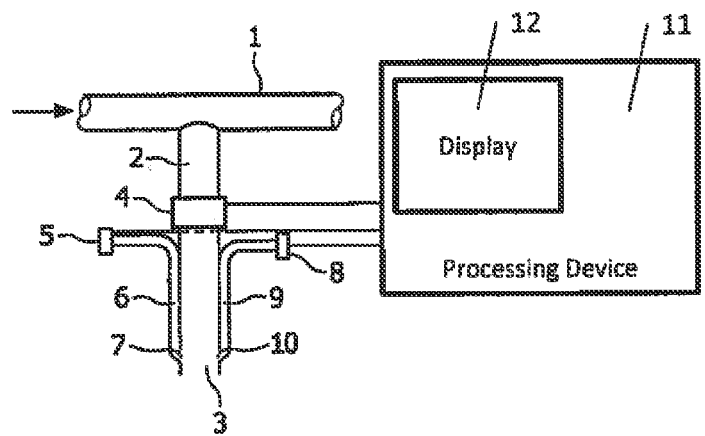
FIG. 4 shows a schematic example of a detail of a ventilation device, according to the invention.

FIG. 4 shows a schematic example of a detail of a ventilation device, according to the invention.

Herein, 1 denotes a gas supply tube, connected to a tracheal tube 2 with an opening 3. A flow meter 4, a first gas concentration meter 5 and a second gas concentration meter 8 are connected to a processing device 11, with a display 12. Many non-shown details, such as gas conditioning devices and so on, may be taken from any known design of ventilation apparatus in the art, as such details are not part of the gist of the present invention.

The first gas concentration meter 5 is connected to the tracheal tube 2 via a first sample tube 6 with a first sampling opening 7, while the second gas concentration meter 8 is connected to the tracheal tube 2 via a second sample tube 9 with a second sampling opening 10.

The flow meter 4 and the first and second gas concentration meters 5, 8 may be any respective suitable measuring devices known in the art. The first gas concentration meter 5 may for example be an O2 meter, while the second gas concentration meter 8 may e.g. be a CO2 meter, without being limited thereto. Furthermore, it is possible to use a single concentration meter device that is able to measure more than one type of gas. The measurements as obtained by the flow meter 4 and the first and second gas concentration meters 5, 8 are received by the processing device 11, such as a computer. The processing device 11 may display the measurements in a spirogram plot on a display 12 and/or output such results in any useful form, such as a data file. This allows a skilled person to perform the method according to the invention. Preferably however, the methods of determining dead spaces and/or synchronising exhaling and inhaling parts of the spirogram are automated, by means of suitable software or suitably programmed or designed hardware, in the processing device 11. The processing device 11 could then, very generally, output a synchronised spirogram, as a display and/or as a data file, and/or it could output one or more values for airway dead space, apparatus dead space, and in particular effective uptake or emission of one or more gases such as oxygen or carbon dioxide.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

The invention claimed is:

1. A method for obtaining and evaluating spirographic data, the method comprising:
   measuring a gas concentration (gc) of a breathing gas mix (Vx) for a plurality of values of a volume of breathing gas mix (Vx) with a spirographic device, the measuring being performed on an inhaled breathing gas mix; and
   determining an apparatus dead space (ApDS) of the breathing gas mix in the spirographic device not taking part in gas exchange by evaluating the measured concentrations of the gc(Vx) as a function of a difference between a volume at a beginning of inhaling and a volume at an end of inhaling of the inhaled breathing gas mix.

2. The method of claim 1, wherein the step of determining the ApDS further includes:
   applying an algorithm to the measured concentrations of the gc(Vx) as a function of the difference between the volume at the beginning of inhaling and the volume at the end of inhaling.

3. The method of claim 2, wherein the algorithm includes:
   determining a first gas concentration (gc(V1)) at a first volume (V1) at the beginning of inhaling;
   determining a second gas concentration (gc(V4)) at a second volume (V4) at the end of inhaling; and
   determining the ApDS as the difference between V1 and a third volume (V2) at which a third gas concentration (gc(V2))=(gc(V1)+gc(V4))/2.

4. The method of claim 1, further including:
   measuring a concentration of a gc(Vx) for a plurality of values of the Vx of an exhaled breathing gas mix; and
   determining an airway dead space (AwDS) or alveolar dead space (AlDS) by evaluating the measured concentration of the gc(Vx) for the plurality of values of the Vx of the exhaled breathing gas mix.

5. The method of claim 3, further including:
   determining a ventilated volume (VV), wherein VV=V1−(ApDS+an airway dead space (AwDS)); and
   determining a ventilation efficiency (VE), wherein as VE=VV/V1.

6. The method of claim 4, further including:
   measuring the concentrations of carbon dioxide and oxygen in the inhaled gas mix and the exhaled gas mix; and
   determining at least one of an ApDS, AwDS and AlDS for a corresponding oxyspirogram and a capnospirogram.

7. The method of claim 3, further including:
   synchronizing an exhaled part and an inhaled part of the spirographic data by matching the exhaled part and the inhaled part at the end of V2 of the spirographic data.

8. A spirographic device for obtaining and evaluating spirographic data, the spirographic device comprising:
   a gas volume meter which measures a volume (Vx) of an exhaled breathing gas mix and an inhaled breathing gas mix;
   a gas measuring probe which measures a gas concentration gc(Vx) of the exhaled breathing gas mix and the inhaled breathing gas mix for a plurality of values of the volume (Vx) of the exhaled breathing gas mix and the inhaled breathing gas mix; and
   a processing unit determines an apparatus dead space (ApDS) of the exhaled breathing gas mix and inhaled breathing gas mix in the spirographic device not taking part in gas exchange by evaluating the measured gas concentrations of the gc(Vx) as a function of a difference between a volume at a beginning of inhaling and a volume at an end of inhaling of the inhaled breathing gas mix.

9. The spirographic device according to claim 8, wherein the spirographic device further comprises:
   a patient ventilation device;
   said patient ventilation device further comprising:
   a tubing adapted to be inserted into a patient's airway; and
   a controllable breathing gas supply connected to said tubing.

10. The spirographic device according to claim 8, wherein the spirographic device further comprises:
    a tubing adapted to be inserted into a patient's airway,
    a controllable breathing gas supply connected to said tubing, the controllable breathing gas supply configured to supply a volume of breathing gas mix to the patient taking into account the determined apparatus dead space (ApDS).

* * * * *